(12) United States Patent
Li et al.

(10) Patent No.: US 7,642,286 B2
(45) Date of Patent: *Jan. 5, 2010

(54) STABLE PHARMACEUTICAL COMPOSITIONS CONTAINING PRAVASTATIN

(75) Inventors: Boyong Li, Morgantown, WV (US); Avinash Nangia, Weston, FL (US); Aaron Dely, Fort Lauderdale, FL (US); David Wong, Milpitas, CA (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 978 days.

This patent is subject to a terminal disclaimer.

(21) Appl. No.: 10/479,932

(22) PCT Filed: Jun. 5, 2002

(86) PCT No.: PCT/US02/17713

§ 371 (c)(1), (2), (4) Date: Apr. 29, 2004

(87) PCT Pub. No.: WO03/000239

PCT Pub. Date: Jan. 3, 2003

(65) Prior Publication Data

US 2005/0165091 A1    Jul. 28, 2005

(51) Int. Cl.
*A61K 31/225* (2006.01)

(52) U.S. Cl. .................................... 514/547

(58) Field of Classification Search ............. 514/547
See application file for complete search history.

(56) References Cited

U.S. PATENT DOCUMENTS

| | | | |
|---|---|---|---|
| 3,983,140 A | 9/1976 | Endo et al. | |
| 4,137,322 A | 1/1979 | Endo et al. | |
| 4,346,227 A | 8/1982 | Terahara et al. | |
| 4,997,658 A * | 3/1991 | Alberts et al. | 424/473 |
| 5,030,447 A | 7/1991 | Joshi et al. | |
| 5,157,025 A | 10/1992 | Aberg et al. | |
| 5,180,589 A | 1/1993 | Joshi et al. | |
| 5,225,202 A | 7/1993 | Hodges et al. | |
| 5,260,305 A | 11/1993 | Dennick | |
| 6,013,281 A | 1/2000 | Lundberg et al. | |
| 6,235,311 B1 * | 5/2001 | Ullah et al. | 424/472 |
| 6,531,507 B1 * | 3/2003 | Pflaum et al. | 514/547 |
| 6,558,659 B2 | 5/2003 | Fox et al. | |
| 6,583,295 B1 | 6/2003 | Pflaum | |
| 6,673,831 B1 | 1/2004 | Tobert | |
| 6,680,341 B1 * | 1/2004 | Kerc | 514/547 |
| 6,806,290 B2 | 10/2004 | Pflaum et al. | |
| 6,838,566 B2 | 1/2005 | Pflaum | |
| 6,911,472 B2 | 6/2005 | Hegde et al. | |
| 2002/0035142 A1 | 3/2002 | Fox et al. | |
| 2002/0055533 A1 | 5/2002 | Kohama et al. | |
| 2003/0152566 A1 | 8/2003 | Schonbeck et al. | |
| 2003/0204105 A1 | 10/2003 | Sugio et al. | |
| 2004/0167085 A1 | 8/2004 | Hedge et al. | |
| 2005/0049422 A1 | 3/2005 | Pflaum | |
| 2005/0053653 A1 | 3/2005 | Kidane et al. | |

FOREIGN PATENT DOCUMENTS

WO    WO 00/33821    6/2000

* cited by examiner

*Primary Examiner*—Kevin Weddington
(74) *Attorney, Agent, or Firm*—Hedman & Costigan, P.C.

(57) ABSTRACT

Stabilized pharmaceutical preparations containing a drug in which is sensitive to a low pH environment, such as pravastatin are disclosed in which pravastatin degradations is prevented with a buffering agent. The basic excipient enhances storage stability.

3 Claims, No Drawings

STABLE PHARMACEUTICAL COMPOSITIONS CONTAINING PRAVASTATIN

BACKGROUND OF THE INVENTION

1. Field of the Invention

A pharmaceutical composition is provided for a medicament which is sensitive to a low pH environment of less than 3, such as pravastatin. Novel, stable oral dosage formulations of pravastatin are provided which include a buffering agent to stabilize and maintain the pH below 9 in an aqueous dispersion. As used in this application, the term pravastatin refers to the free base form of the drug as well as the pharmaceutically acceptable salts such as pravastatin sodium.

2. Description of the Related Art

Pravastatin sodium, designated chemically as [1S-[1α(β$S^*$,δ$S^*$), 2α, 6α, 8β-($R^*$),8aα]]-1,2,6,7,8,8a-hexahydro-β,δ,6-trihydroxy-2-methyl-8-(2-methyl-1-oxobutoxy)-1-naphthaleneheptanoic acid monosodium salt is a hydroxymethylglutaryl-CoA (HMG-CoA) reductase inhibitor antilipemic agent described in U.S. Pat. No. 4,346,227. It is indicated in hypercholesterolemic patients for primary prevention of coronary events including myocardial infarction (MI); to reduce the risk of undergoing myocardial revascularization procedures; to reduce the risk of cardiovascular mortality. It is indicated in hypercholesterolemic patients for secondary prevention of cardiovascular events, including MI and to slow the progression of coronary arteriosclerosis. Pravastatin is also used as an adjunct to diet for the reduction of elevated total- and LDL-cholesterol and triglyceride levels in patients with primary hypercholesterolemia and mixed dyslipidemia (Types IIa and IIb). The agent specifically competitively inhibits 3-hydroxy-3-methyl-glutaryl-coenzyme A (HMG-CoA) reductase, the enzyme that catalyzes the conversion of HMG-CoA to mevalonate, which is an early rate-limiting step in cholesterol biosynthesis. HMG-CoA reductase inhibitors increase HDL cholesterol and decrease LDL cholesterol, VLDL and plasma triglycerides. The usual dosing regimen is 10-40 mg once daily at bedtime.

Certain drugs require an alkaline environment for the purposes of stability. Stability requirements are covered in the United States Pharmacopoeia (U.S.P.), in the Good Manufacturing Practices (GMPs) as well as in FDA Guidelines for stability studies. Buffers may be added to increase stability of certain pharmaceuticals. Buffers may also increase the thermo stability of drug in formulations that require drying during the process of producing the final dosage form.

Pravastatin sodium is relatively polar hydrophilic, acid labile, and degrades to form its lactone and various isomers. Degradation results in lower bioavailability of pravastatin sodium. Pravastatin sodium requires a buffer to enhance storage stability. Strategies used in the prior art to stabilize pravastatin sodium formulations include: addition of a basifying agent to raise the pH to at least 9, and packaging of the product in a manner to decrease exposure to moisture.

The stability of pravastatin sodium is affected by factors including formulation and storage conditions. Pravastatin sodium is known to be an acid labile compound. Labeling of pravastatin sodium tablets indicates storage at a temperature not to exceed 30° C. and protection from light and moisture.

Stabilization is achieved by basification of the environment in which degradation occurs. Stabilized compositions in the prior art have a pH of 9 or over in an aqueous dispersion. The amounts of basifying agent range from 1 to 75%. Basifying agents used include magnesium oxide. Patents such as U.S. Pat. Nos. 5,180,589, 6,235,311, 5,225,202, 5,030,447 (which are incorporated herein by reference) describe aluminum oxide, all alkali metal hydroxides such as sodium hydroxide, potassium hydroxide or lithium hydroxide, or alkaline earth metal hydroxides such as calcium, magnesium, aluminum hydroxide, dihydroaluminum sodium carbonate, aluminum magnesium hydroxide sulfate, aluminum hydroxide magnesium carbonate co-dried gel, or ammonium hydroxides, calcium carbonate, magnesium carbonate, magnesium stearate, piperazine, sodium acetate, sodium citrate, sodium tartrate, sodium maleate, sodium succinate and mixtures thereof. Stabilization of the commercially available pravastatin sodium (Pravacol®) is achieved by basification by magnesium oxide which imparts a pH above 9, preferably about 10.

Although the prior art basifying agents can prevent the degradation of pravastatin sodium, they are less desirable because some are strong bases which may have an adverse effect on excipients used with pravastatin sodium pharmaceutical compositions. For example, lactose discolors and emits a caramelized odor in the presence of certain basifying agents, for example piperazine. Additionally, the high alkalinity occurring at dissolution of these formulations may disrupt the acidic pH milieu of the gastrointestinal (GI) mucosa and is problematic for patients with pre-existing GI mucosal damage.

The need exists for a stable pravastatin formulation prepared from an aqueous dispersion of hydrophobic polymers. Such formulations have a practical application, and represent a valuable contribution to the medical arts. The present invention provides such compositions, and offers efficient and cost effective methods of preparation.

SUMMARY OF THE INVENTION

The present invention meets the unfulfilled needs of the pharmaceutical industry.

The forgoing objectives are met by a pharmaceutical composition in the form of a tablet which has enhanced stability comprising:
 (a) pravastatin;
 (b) a filler;
 (c) a binder;
 (d) a buffering agent, and
 (e) a disintegrant wherein the pH of the composition is less than 9.

The pharmaceutical formulation of the present invention is a solid dosage form of a medicament having a unique buffer system which results in excellent stability. Specifically, the current invention is directed to stable oral formulations of a medicament sensitive to a low pH environment, such as pravastatin, one or more fillers such as anhydrous lactose, mannitol, one or more binders, such as microcrystalline cellulose, polyvinylpyrrolidine (PVP), one or more disintegrants, such as croscarmellose sodium, one or more lubricants, such as magnesium stearate, one or more coloring agents, such as purple Lake, and one or more buffering agents, such as tromethamine or sodium phosphate dibasic to impart a pH to an aqueous dispersion of the composition of less than 9.0, preferably less than 8.5, and most preferably less than 8.0.

A preferred formulation can be made by addition of tromethamine or sodium phosphate dibasic in a range of 1-10%, preferably 2-5%, as a buffering agent which imparts an increase in localized pH within the composition. This increase in localized pH prevents the pravastatin from degrading to form its lactone and various other isomers. The pH of the aqueous dispersion of the composition is about 8 but does not exceed 9 in an aqueous environment. The composition also exhibits excellent stability when stored under accelerated conditions of 40° C. and 75% relative humidity.

Accordingly, it is an object of this invention to provide a novel and useful pravastatin formulation which is stable in a low pH environment. This represents an unexpected improvement in the art and substantially overcomes the disadvantages known to the prior art.

It is also an object of the present invention to provide both a method of stabilizing pravastatin sodium to slow the degradation thereof and provide products that can be stored for long periods of time at room temperature, i.e. under humidity and temperature conditions usually encountered in pharmacies and medicine cabinets. It is a further object to provide solid oral pravastatin sodium dosage forms where the amount of active drug will be prevented from being reduced to less than 90% of its labeled strength, and more preferably not less than 95% of the labeled strength after one year of storage under controlled room temperature conditions.

Other objects, features and advantages of the invention are not taught in the prior art but will be more apparent to those versed in the art from the following specification, taken in conjunction with the accompanying claims.

DETAILED DESCRIPTION OF THE PREFERRED EMBODIMENTS

In accordance with the present invention, a pharmaceutical composition is provided which includes a medicament which may degrade in a low pH environment but which is prevented from doing so by the addition of a buffering agent. Accordingly, the pharmaceutical composition of the invention includes drugs which are chemically unstable in an acidic environment, such as pravastatin sodium.

The invention provides immediate release pravastatin formulations which provide alternatives to the prior art formulations which require the presence of a basifying agent which have a pH of at least 9.

Unlike the prior art basifying agent requirement, the invention favorably influences stability by the addition of a buffer which can be an alkaline reacting organic compound, a hydroxide of an alkali metal, an alkaline salt of phosphoric acid, carbonic acid or silicic acid or an alkaline ammonium salt Representative examples of these buffers are described in U.S. Pat. No. 6,013,281 which is incorporated herein by reference. Basifying agent, as the term is used herein, refers to compounds capable of raising the pH to above 7. They are added to formulations of pravastatin to improve chemical and physical stability. According to previous pravastatin formulations containing basifying agents, tablets should retain 80-90% of active ingredient at the end of one year in the presence of stabilizers.

The stability of these formulations without a basifying agent was tested in accordance with and exceeding current pharmaceutical industry standards for storage (i.e., 4 to 12 weeks at about 40° C. and about 75% relative humidity). Formulations of the present invention stored under these conditions retain at least 90% of the pravastatin in the composition at the time of storage. Standard procedures such as HPLC or UV spectroscopic methods may be used to determine the amount of active ingredient remaining after storage. The final dosage form most preferably retains assay limits of 90 to 110 percent of the original assay value when stored under controlled room temperature conditions. The design of the stability studies was in compliance with the general requirements suggested by the FDA stability guidelines.

The total amount of inactive ingredients in the formulations is preferably 30% or more of the weight of the pravastatin. The tablets are prepared by the direct compression method.

The invention is particularly adaptable to pharmaceutical compositions containing pravastatin. Pharmaceutical compositions of the present invention generally contain 10-40 mg or an amount with the range of about 2 to about 50% of pravastatin by weight, and preferably from about 4 to about 25% by weight of the composition. More preferred compositions of the invention contain 40 mg of active ingredient and may be in the form of tablets, caplets or capsules.

The pharmaceutical formulations of the present invention provide a stable environment for drugs which require an alkaline environment by utilizing a buffer. The formulations contain a buffering agent present in an amount within the range of about 3 to about 10% by weight of the composition. Examples of other suitable buffering agents include sodium acetate, sodium citrate, sodium tartrate, sodium fumerate, sodium maleate, sodium succinate, combinations of sodium or potassium hydroxide with sodium or potassium acid phosphate.

The preferred buffering agent is tromethamine, a weak base amino-alcohol, also known as 2-amino-2 hydroxymethyl-1,3-propanediol, (tris(hydroxymethyl)aminomethane) or TRIS. Tromethamine has a greater buffering capacity than bicarbonate; pKa 7.82 versus 6.1, respectively. Tromethamine has been found to have excellent stabilizing effects on solid dosage forms containing drugs with limited water solubility which need to be solubilized in buffer to avoid otherwise solubilizing the drug in large quantities of granulating media. Tromethamine has been discovered to be most advantageous when a therapeutically-effective buffer-soluble drug has a solubility at 25° C. of less than 1 mg of drug per ml of water at pH 7.0 or lower. An advantage of tromethamine lies in its water solubility and, accordingly, it blends well with an excipient like lactose. Tromethamine as used herein is preferably present in the range of about 1 to 10%, more preferably, 2 to about 6% of the pravastatin sodium drug granulation, and most preferably, 4% by weight of the composition.

Another preferred buffering agent is dibasic sodium phosphate ($Na_2HPO_4$), which is very soluble in water and widely used as a buffering agent for pharmaceuticals.

Pharmaceutical compositions of the present invention as in Example 1 below, may contain one or more fillers in a range from about 30 to about 95% by weight and preferably from about 60 to about 80% by weight. Anhydrous lactose which is considered an inert pharmaceutical excipient is added as a directly compressible tableting excipient. Anhydrous lactose is also used as a diluent to achieve content uniformity of the finely divided active ingredients. The release rate of anhydrous lactose increases as the particle size of the sugar decreases. In the preferred embodiment, the optimal amount of lactose is found to be 73 weight % of the granules and 73% of the total tablet weight. Examples of other suitable excipients known to those skilled in the art which may be used include, sucrose, dextrose, lactose, cellulose derivatives such as microcrystalline cellulose, calcium carbonate, calcium sulfate, magnesium carbonate, corn starch, modified corn starch, mannitol, xylitol, fructose, sorbitol, and mixtures thereof. The optimal concentration of the fillers for pravastatin granules was determined to be a mixture of 1:6.5 (wt./wt.). The optimal concentration of the fillers for the pravastatin sodium tablets was determined to be a mixture of 1:3.

An effective amount of any generally accepted pharmaceutical tableting lubricant, may be added to compress the tablets. If a lubricant is added it should be present in an amount within the range from about 0.05 to about 6%, preferably 0.5 to about 2% by weight may be added. Tablet lubricants present are preferably from the group consisting of glyceryl monostearates, magnesium stearate, palmitic acid, talc, carnauba wax, calcium stearate, sodium or magnesium lauryl sulfate, calcium soaps, zinc stearate, polyoxyethylene monostearates, calcium silicate, silicon dioxide, hydrogenated vegetable oils and fats, or stearic acid. Most preferably, magnesium stearate is present as a lubricant to prevent the powder from agglomerating during processing on a high speed rotary press. Magnesium stearate is added to the granulation to assist compression. A preferred lubricant is magnesium stearate. In the preferred embodiment shown in Example 1, magnesium stearate is used in an amount of less than 2% of the tablet.

One or more binders may be present in a range of about 0-20%, preferably 5 to about 15%, and most preferably about 10%. Examples of suitable binders may include, but are not limited to cellulose compounds, (such as microcrystalline cellulose, methyl cellulose, hydroxymethyl cellulose, hydroxypropyl methyl cellulose), acrylates, methacrylates, polyvinylpyrrolidone, and other materials known to have cohesive and desirable binding properties which are known to one of ordinary skill in the art. In the preferred embodiment, microcrystalline cellulose is used.

A tablet disintegrant is added to the direct compression process for its wicking (i.e., the ability of particles to draw water into the porous network of a tablet) and swelling ability. Some of these disintegrants also serve as excellent binders and are able to substantially improve the mechanical strength of the formulation. Suitable disintegrants are carboxymethyl cellulose sodium, carboxymethyl cellulose calcium, crospovidone, sodium starch glycolate, corn starch, insoluble cationic-exchange resins such as polyacrylin, microcrystalline cellulose, croscarmellose. Disintegrants are added at concentrations ranging from 0.5-10%. Croscarmellose sodium (cross-linked carboxymethyl cellulose) preferably at a concentration of 2-6%, and most preferably at a concentration of 5% is preferred. Croscarmellose is not compatible with hygroscopic excipients and soluble salts of metals.

A colorant may be added to the lactose forming the pravastatin sodium granules and the directly compressed powders. Alternatively, colorant may be added to the tableting process. The colorant may include various soluble synthetic dyes and insoluble pigments such as FD&C colors including aluminum lakes. In the preferred embodiment, Lake blend purple is utilized.

The tablets of the invention may also include a film or sugar coating layer. The film or sugar coating influences the tablet moisture, surface roughness, and coating efficacy and uniformity. The film or sugar coating formulation which may be 1-6% of the total formulation.

In a preferred embodiment the pravastatin is granulated with the filler, the binding agent and the buffer solution. The pravastatin granules preferably comprise 50-90% of the total tablet weight, more preferably 60-80%, and most preferably 70-75%. The preferred pravastatin granule composition of the invention is given below:

Pravastatin Granules

| Ingredient | Weight % granules | Weight % tablet |
| --- | --- | --- |
| Pravastatin | 5-25 | 1-20 |
| Filler | 30-90 | 50-90 |
| Buffering Agent | 1-10 | 2-6 |
| Disintegrant | 0-20 | 5-15 |

The pH there granules should be less than 9, preferably less than 8.5 and most preferably less than 8.

The manufacture of tablets of the present invention involves dissolving tromethamine in water and using the solution to granulate a mixture of anhydrous lactose, microcrystalline cellulose, and pravastatin.

Filler (preferably anhydrous lactose) and binder (preferably microcrystalline cellulose) are separately screened or milled to break up agglomerates. The screened materials and drug (pravastatin) are then granulated in the following order: fraction of the filler (less than 50%), drug, binder, remaining filler (less than 40%). A buffer in solution is added and mixed. Granulation cycle is initiated until the desired consistency of granulation is achieved. The granules are then passed through a 25 mesh screen, dried by conventional methods and passed through a Fitzmill. The drug granulation is then blended with sufficient quantity of filler to bulk up for tablet compression. The filler is screened through a 25 mesh screen. The drug granules are placed into a blender with screened filler. The lubricant is then screened and added to the blender followed by the coloring agent which is screened and added to the blender.

The powders are then compressed into tablets using appropriate conventional tools such as a suitable tableting press to form the tablet of the invention. Each tablet in the above procedure preferably contains a therapeutically effective amount of pravastatin sodium and the following excipients:

Pravastatin Tablets

|  | Weight %/Tablet |
| --- | --- |
| Pravastatin granules | 50-80 |
| Filler | 10-25 |
| Disintegant | 0.5-10 |
| Lubricant | 0.5-2 |

Alternatively, the tablets may also be formulated by a wet granulation technique where a mixture of the medicament, buffer, filler, and binder is granulated using an aqueous binder solution such as polyvinyl pyrrolidone.

The following examples are illustrative of the present invention, and the examples should not be considered as limiting the scope of this invention in any way, as these examples and other equivalents thereof win become apparent to those versed in the art in the light of the present disclosure, and the accompanying claims.

EXAMPLE 1

Tablet formulations containing 40 mg of pravastatin sodium are made with the following ingredients in the following amounts:

Granules

| INGREDIENT | PERCENT BY WEIGHT |
|---|---|
| Pravastatin sodium | 13.33 |
| Anhydrous lactose, NF | 37.67 |
| Anhydrous lactose, NF | 35.00 |
| TRIS (Tromethamine), USP | 4.00 |
| Microcrystalline cellulose, NF | 10.00 |

The composition is made in the following manner:

Tromethamine is dissolved in purified water.

Two seperate portions of anhydrous lactose, along with microcrystalline cellulose are individually sifted through a 25 mesh screen. The sifted ingredients are then placed in a granulator in the following order:

1. The larger portion of anhydrous lactose
2. pravastatin sodium
3. microcrystaline cellulose
4. the smaller portion of anhydrous lactose After each addition, the granulator is started and allowed to mix the dry materials. After, the addition of the final portion of anhydrous lactose, the material is granulated with tromethamine solution, using conventional means. The granulate is dryed in any acceptable manner for pharmaceutical processing. Drying continues until the moisture content is below about 2%. Most preferably, the granules are dryed until the moisture content is below about 1.8%. The dried granules are passed through a screen of 25 mesh approximate size. The screening of the granules may be through any desired machine or mechanism as is commonly known in the art.

Tablets

A pharmaceutical formulation is then prepared as follows using the pravastatin granules comprising approximately, by weight:

| INGREDIENT | PERCENT BY WEIGHT |
|---|---|
| pravastatin sodium granules | 75 |
| anhydrous lactose | 18 |
| croscarmellose sodium, NF | 5 |
| magnesium stearate | 1 |
| lake blend purple | 1 |

After screening the anhydrous lactose, it is charged together with the pravastatin granules into a suitable blender. After sifting through a 25 mesh screen, the resultant granulation is then lubricated. In the following order, croscarmellose sodium, magnesium stearate, and Lake Blend Purple are added to the blender. The blend was compressed into tablets using any conventional manner.

EXAMPLE 2

In the same manner as described in Example 1, a tablet containing 20 mg of pravastatin sodium is made with the ingredients and amounts indicated below:

Granules

| INGREDIENT | MG/TABLET |
|---|---|
| Pravastatin sodium | 22 |
| Anhydrous lactose, NF | 75 |
| Anhydrous lactose, NF | 70 |
| TRIS (Tromethamine), USP | 8 |
| Microcrystalline cellulose, NF | 20 |

Tablets

| INGREDIENT | MG/TABLET |
|---|---|
| pravastatin sodium granules | 200 |
| anhydrous lactose | 36 |
| croscarmellose sodium, NF | 10 |
| magnesium stearate | 2 |
| lake blend purple | 2 |

EXAMPLE 3

In the same manner as described in Example 1, a tablet containing 10 mg of pravastatin sodium is made with the ingredients and amounts indicated below:

The tabletting is performed by the following steps:
1. Pass the anhydrous lactose through a 25 mesh screen.
2. Combining the screened lactose with the pravastatin sodium granules into a suitable blender.
3. Allowing the blender to combine the granules with lactose until a uniform blend is achieved.
4. Pass the crosscarmellose sodium, magnesium stearate, and Lake Blend Purple through a 25 mesh screen.
5. Add the crosscarmellose sodium, magnesium stearate, and Lake Blend Purple to the blender containing the granules with lactose.
6. Allow to blend until uniformity is achieved.
7. Compress into tablets.

The pH of this tablet is approximately 8.35 and was determined by dissolving 1 tablet in 900 ml of deionized water.

Granules

| INGREDIENT | MG/TABLET |
|---|---|
| Pravastatin sodium | 11 |
| Anhydrous lactose, NF | 38 |
| Anhydrous lactose, NF | 35 |
| TRIS (Tromethamine), USP | 4 |
| Microcrystalline cellulose, NF | 10 |

The pH of this tablet is approximately 8.00 and was determined by dissolving 1 tablet in 900 ml of deionized water.

Tablets

| INGREDIENT | MG/TABLET |
|---|---|
| pravastatin sodium granules | 100 |
| anhydrous lactose | 18 |
| croscarmellose sodium, NF | 5 |

| INGREDIENT | MG/TABLET |
|---|---|
| magnesium stearate | 1 |
| lake blend purple | 1 |

Tablet Stability

Pravastatin sodium tablets with tromethamine were subjected to an accelerated stability test The tablets were exposed to 40° C. (75% relative humidity) for 3 months time. At the end of 3 months time, the amount of pravastatin sodium that had degraded to lactones were determined by HPLC analysis.

The stability tests indicate that replacing the basifying agent magnesium oxide with the buffer tromethamine increases the stability of pravastatin sodium tablets.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications and variations may be made herein, in accordance with the inventive principles disclosed, without departing from the spirit and scope of the invention.

We claim:

1. A pharmaceutical tablet consisting essentially of a compressed mixture of:
   (a) 2-50 weight percent pravastatin sodium;
   (b) 30-95 weight percent of a filler;
   (c) 0-20 weight percent of a binder;
   (d) 1-10 weight percent of tromethamine;
   (e) 0.5-10 weight percent of a disintegrant; and
   (f) 0-6 weight percent of a lubricant wherein said tromethamine is present in an amount that allows the tablet to retain 90 to 110 percent of an original pravastatin assay value after storage for 3 months at about 40° C. and 75% relative humidity and said tromethamine is present in an amount such that the pH of the tablet is less than 9 as determined by dissolving the composition in 900 ml of deionized water.

2. The tablet as defined in claim 1 wherein the tablet retains not less than 95% of the original pravastatin value after storage for 3 months at about 40° C. and 75% relative humidity.

3. The tablet as defined in claim 1 wherein the tromethamine is present in an amount such that the pH of the tablet is about 8 and does not exceed 9.

* * * * *